(12) United States Patent
Mizukura et al.

(10) Patent No.: US 11,324,404 B2
(45) Date of Patent: May 10, 2022

(54) KINESITHERAPY APPARATUS AND ANAEROBIC THRESHOLD IDENTIFYING METHOD

(71) Applicant: MITSUBISHI ELECTRIC ENGINEERING COMPANY LIMITED, Tokyo (JP)

(72) Inventors: Isao Mizukura, Tokyo (JP); Tomohiko Kisaka, Torrance, CA (US)

(73) Assignee: MITSUBISHI ELECTRIC ENGINEERING COMPANY, LIMITED, Tokyo (JP)

( * ) Notice: Subject to any disclaimer, the term of this patent is extended or adjusted under 35 U.S.C. 154(b) by 516 days.

(21) Appl. No.: 15/682,975

(22) Filed: Aug. 22, 2017

(65) Prior Publication Data

US 2018/0235479 A1 Aug. 23, 2018

(30) Foreign Application Priority Data

Feb. 23, 2017 (JP) .............................. JP2017-031874

(51) Int. Cl.
*A61B 5/0205* (2006.01)
*A63B 23/04* (2006.01)
(Continued)

(52) U.S. Cl.
CPC ........ *A61B 5/0205* (2013.01); *A61B 5/02125* (2013.01); *A61B 5/221* (2013.01);
(Continued)

(58) Field of Classification Search
CPC ........... A61B 5/00; A61B 5/02; A61B 5/0205; A61B 5/22–221; A61B 5/021–02125;
(Continued)

(56) References Cited

U.S. PATENT DOCUMENTS

| 5,165,278 | A | * | 11/1992 | Huszczuk | .............. | A61B 5/221 |
| | | | | | | 482/900 |
| 5,410,472 | A | * | 4/1995 | Anderson | ........ | A63B 21/00181 |
| | | | | | | 482/9 |

(Continued)

OTHER PUBLICATIONS

Frikha, M., N. Chaari, N. Mezghanni, and N. Souissi. "Influence of warm-up duration and recovery interval prior to exercise on anaerobic performance." (2016). Biology of Sport, vol. 33, No. 4. (Year: 2016).*

*Primary Examiner* — Rachel T Sippel
*Assistant Examiner* — Jacqueline M Pinderski
(74) *Attorney, Agent, or Firm* — Rothwell, Figg, Ernst & Manbeck, P.C.

(57) ABSTRACT

A kinesitherapy apparatus includes a measuring instrument, a pedaled rotational mechanism, a rotating electrical machine configured to apply an assist load, which is a regenerative load or a power running load, to the pedaled rotational mechanism, and a motion control device. The motion control device performs power running operation of the rotating electrical machine so that a minus assist load is generated in a warm-up period. In a ramp loading period following the warm-up period, the motion control device raises the assist load from the minus assist load, and calculates an anaerobic threshold based on time-series data of oxygen uptake and carbon dioxide emission that are obtained via the measuring instrument.

10 Claims, 4 Drawing Sheets

(51) Int. Cl.
*A63B 22/02* (2006.01)
*A61B 5/021* (2006.01)
*A63B 22/06* (2006.01)
*A61B 5/22* (2006.01)

(52) U.S. Cl.
CPC ........ *A63B 22/025* (2015.10); *A63B 22/0605* (2013.01); *A63B 23/0476* (2013.01); *A61B 2505/09* (2013.01); *A61B 2576/023* (2013.01); *A63B 2220/58* (2013.01); *A63B 2220/62* (2013.01); *A63B 2220/836* (2013.01)

(58) Field of Classification Search
CPC .......... A61B 2576/023; A61B 2505/09; A63B 22/00; A63B 22/06–0605; A63B 22/02; A63B 22/0235–025; A63B 23/00; A63B 23/035; A63B 23/04; A63B 23/0476; A63B 2220/836; A63B 2220/62; A63B 2220/58
See application file for complete search history.

(56) References Cited

U.S. PATENT DOCUMENTS

| | | | |
|---|---|---|---|
| 5,782,772 A * | 7/1998 | Stegmann | A61B 5/7239 600/483 |
| 6,512,948 B1 * | 1/2003 | Shiga | A61B 5/024 600/520 |
| 6,942,603 B1 * | 9/2005 | Tsai | A63B 21/00181 482/5 |
| 9,737,761 B1 * | 8/2017 | Sivaraj | A61B 5/7275 |

* cited by examiner

KINESITHERAPY APPARATUS AND ANAEROBIC THRESHOLD IDENTIFYING METHOD

BACKGROUND OF THE INVENTION

1. Field of the Invention

The present invention relates to a kinesitherapy apparatus and an anaerobic threshold identifying method, which are used in an exercise stress test to calculate an anaerobic threshold (AT) or an anaerobic metabolic threshold, which is an index of exercise tolerance.

2. Description of the Related Art

For example, some kinesitherapy apparatus are capable of helping a physically handicapped person or an elderly person who undergoes kinesitherapy recover motor function and maintain physical strength with the use of a pedaling motion (see Japanese Patent No. 3929230, for example). This type of kinesitherapy apparatus is called an ergometer.

In recent years, the AT is obtained as an index of exercise tolerance through an exercise stress test that is conducted in combination with an intake gas analysis, and the obtained AT is used to prescribe exercise and determine the effect of treatment, for example. Ergometers are employable in such exercise stress tests as well.

The advantages of employing an ergometer in an exercise stress test are as follows:

Load adjustment is easy, setting of a constant load is a selectable option, and an external load can be quantified with accuracy. As a result, the relation of the exercise intensity to the ventilation volume (VE), the oxygen uptake ($VO_2$), and the carbon dioxide emission ($VCO_2$) can be evaluated.

The body posture of a person to be tested pedaling on an ergometer changes little. Various measurements can consequently be conducted with ease.

When the amount of oxygen taken into the body in one minute per kilogram (kg) in body weight is expressed in milliliters, for example, the "oxygen uptake" is expressed by the following expression.

$$\dot{V}O2$$

The symbol of the unit of the oxygen uptake is really a "V dot", which is V with an overhead dot. However, the symbol of the unit of the oxygen uptake and other units to be noted by the symbol "V dot" are herein simply noted by "V".

How to calculate the AT is now described. Ramp loading, which is commonly used in a method of calculating the AT with the use of an ergometer, is described through the V-slope method and through one of trend methods that uses $VE/VO_2$ and $VE/VCO_2$. In an ergometer where setting of a constant load is a selectable option as described above, a load intensity can easily be set for each of a resting period, a warm-up period, a ramp loading period, and a cooling down period when the exercise stress test is carried out. A constant amount of increase in load per unit time is set to the ramp loading period. With the V-slope method, the AT of a person to be tested can be obtained by calculating the minute oxygen uptake ($VO_2$) and the minute carbon dioxide emission ($VCO_2$) from the measurement of the oxygen uptake and carbon dioxide mission per breath in the ramp loading period. With one of trend methods that uses $VE/VO_2$ and $VE/VCO_2$, the AT of a person to be tested can be obtained by calculating the minute ventilation volume (VE), the minute oxygen uptake ($VO_2$), and the minute carbon dioxide emission ($VCO_2$) from the measurement of the ventilation volume per breath, in addition to the oxygen uptake and carbon dioxide emission per breath used in the method described above, in the ramp loading period.

Specifically, the AT is calculated based on a concept described below. The minute oxygen uptake ($VO_2$) during ramp loading increases linearly. The minute carbon dioxide emission ($VCO_2$) and the minute ventilation volume (VE), on the other hand, change non-linearly in high-intensity exercise while increasing linearly in low-intensity exercise.

"High-intensity exercise" means an exercise intensity that exceeds the AT. When the exercise intensity exceeds the AT, the glycolytic system (anaerobic metabolism) comes into play in order to produce necessary energy, and lactic acid generation increases. The lactic acid is buffered in a cell, thereby liberating carbon dioxide ($CO_2$). The liberated carbon dioxide joins carbon dioxide that is produced by aerobic metabolism, which makes the proportion of increase of $VCO_2$ higher. The value of $VCO_2$ in high-intensity exercise is therefore larger than a value along an extension of a straight line that represents $VCO_2$ before the AT is reached, and accordingly changes in a non-linear fashion.

Immediately after the exercise intensity exceeds the AT, the minute ventilation volume VE increases in parallel with $VCO_2$, and $VE/VO_2$ therefore increases. On the other hand, $VE/CO_2$ does not change because metabolic acidosis is not in progress on the whole-body scale, which means no hyperventilation with respect to $CO_2$.

A characteristic change in gas exchange before and after the AT is reached occurs in this manner. With one of trend methods that uses $VE/VO_2$ and $VE/VCO_2$, for example, a point at which $VE/VCO_2$ does not increase but $VE/VO_2$ increases can therefore be obtained as the AT from the transitions of the measurement values with time during ramp loading. With the V-slope method, $VCO_2$ is substantially equal in amount (ml/min.) to $VO_2$ before the AT is reached but begins to increase and turns into a value larger than $VO_2$ after the AT is reached, and hence the point of inflection, or the point of turning, of $VCO_2$ can be obtained as the AT.

An ergometer of the related art obtains the AT from the result of measuring the minute ventilation volume (VE), the minute oxygen uptake ($VO_2$), and the minute carbon dioxide emission ($VCO_2$) in a loading period that follows a warm-up period where the load is constant at, for example, 20 watt (W) and that increases the load at a constant slope, for example, 10 W/min., as ramp loading.

The ergometer of the related art ensures that the AT can be calculated for a person with low physical strength whose AT is at a point where the load is less than 20 W by controlling the load so that a ramp loading period follows a warm-up period where the load is set to 0 W.

The related art, however, has the following problem.

As described above, cardiopulmonary exercise testing by the method of the related art calculates the AT by using a constant load, for example, 20 W or 0 W, for a warm up to stabilize the minute oxygen uptake and the minute carbon dioxide emission, and then executing ramp loading.

With this method of the related art, the minute oxygen uptake of a patient who has heavy lower limbs, for example, an obese patient, in the warm-up period is large in terms of metabolism compared to the minute oxygen uptake during a rest, because even a warm up at a load of 0 W causes internal respiration in muscles due to voluntary muscle activity. This results in a failure to obtain a sufficient number of measurement points where the minute oxygen uptake and the minute carbon dioxide emission are estimated in the ramp loading period from the start of ramp loading until the AT is reached, and the failure gives rise to a problem of diminished precision in AT calculation.

The failure to obtain a sufficient number of points at which the minute oxygen uptake and the minute carbon dioxide emission are estimated in the ramp loading period occurs also when the person to be tested is a person with low physical strength whose AT corresponds to a relatively light load. The resultant problem is that the AT is calculated with diminished precision or cannot be identified.

SUMMARY OF THE INVENTION

The present invention has been made to solve the problem described above, and an object of the present invention is therefore to provide a kinesitherapy apparatus and an anaerobic threshold identifying method with which a stable AT can be calculated for any person to be tested.

According to one embodiment of the present invention, there is provided a kinesitherapy apparatus, including: a measuring instrument configured to measure oxygen uptake and carbon dioxide emission of a person to be tested; a pedaled rotational mechanism to be operated by the person to be tested; a rotating electrical machine, which is linked to the pedaled rotational mechanism via a transmission mechanism, and is configured to apply an assist load, which is one of a regenerative load and a power running load, to the pedaled rotational mechanism by switching between regenerative operation and power running operation; and a motion control device configured to drive and control the rotating electrical machine so that the assist load is applied as programmed by an exercise stress program that is suited to the person to be tested, in which the motion control device is configured to perform, when an anaerobic threshold (AT) is calculated by conducting a kinesitherapy test on the person to be tested, the power running operation of the rotating electrical machine so that a minus assist load is generated in a warm-up period, decrease the assist load and increase the regenerative load at a constant proportion in a continuous manner from the minus assist load to the regenerative load in a ramp loading period, which follows the warm-up period, and enable the kinesitherapy apparatus to calculate the anaerobic threshold based on time-series data of respiratory metabolism including the oxygen uptake, the carbon dioxide emission, and ventilation volume, which is obtained via the measuring instrument during the ramp loading period.

Further, according to one embodiment of the present invention, there is provided an anaerobic threshold identifying method for calculating an anaerobic threshold by conducting a kinesitherapy test on a person to be tested with a kinesitherapy apparatus, the kinesitherapy apparatus including: a measuring instrument configured to measure oxygen uptake and carbon dioxide emission of the person to be tested; a pedaled rotational mechanism to be operated by the person to be tested; a rotating electrical machine, which is linked to the pedaled rotational mechanism via a transmission mechanism, and is configured to apply an assist load, which is one of a regenerative load and a power running load, to the pedaled rotational mechanism by switching between regenerative operation and power running operation; and a motion control device configured to drive and control the rotating electrical machine so that the assist load is applied as programmed by an exercise stress program that is suited to the person to be tested, the anaerobic threshold identifying method, which is executed by the motion control device, including: a first step of performing the power running operation of the rotating electrical machine so that a minus assist load is generated in a warm-up period before the anaerobic threshold is calculated; a second step of raising a load in a ramp loading period, which follows the warm-up period, from the minus assist load at a constant proportion, and obtaining time-series data of the oxygen uptake and time-series data of the carbon dioxide emission in the ramp loading period via the measuring instrument; and a third step of obtaining one of a point of inflection and a point of turning by creating a two-dimensional coordinate graph of minute oxygen uptake and minute carbon dioxide emission based on the time-series data obtained in the second step, and calculating a load value that corresponds to one of the point of inflexion and the point of turning as the anaerobic threshold.

According to the present invention, the kinesitherapy apparatus and the anaerobic threshold identifying method include the configuration to calculate the AT from time-series measurement data of the minute oxygen uptake and time-series measurement data of the minute carbon dioxide emission that are collected in the ramp loading period, by starting the ramp loading period from a state where a power running current larger than one equivalent to mechanical friction is caused to flow. The resultant kinesitherapy apparatus and anaerobic threshold identifying method are capable of calculating a stable AT for any person to be tested.

DESCRIPTION OF THE EMBODIMENTS

A kinesitherapy apparatus and an anaerobic threshold identifying method according to a preferred embodiment of the present invention is described below with reference to the accompanying drawings.

First Embodiment

Figure 1:
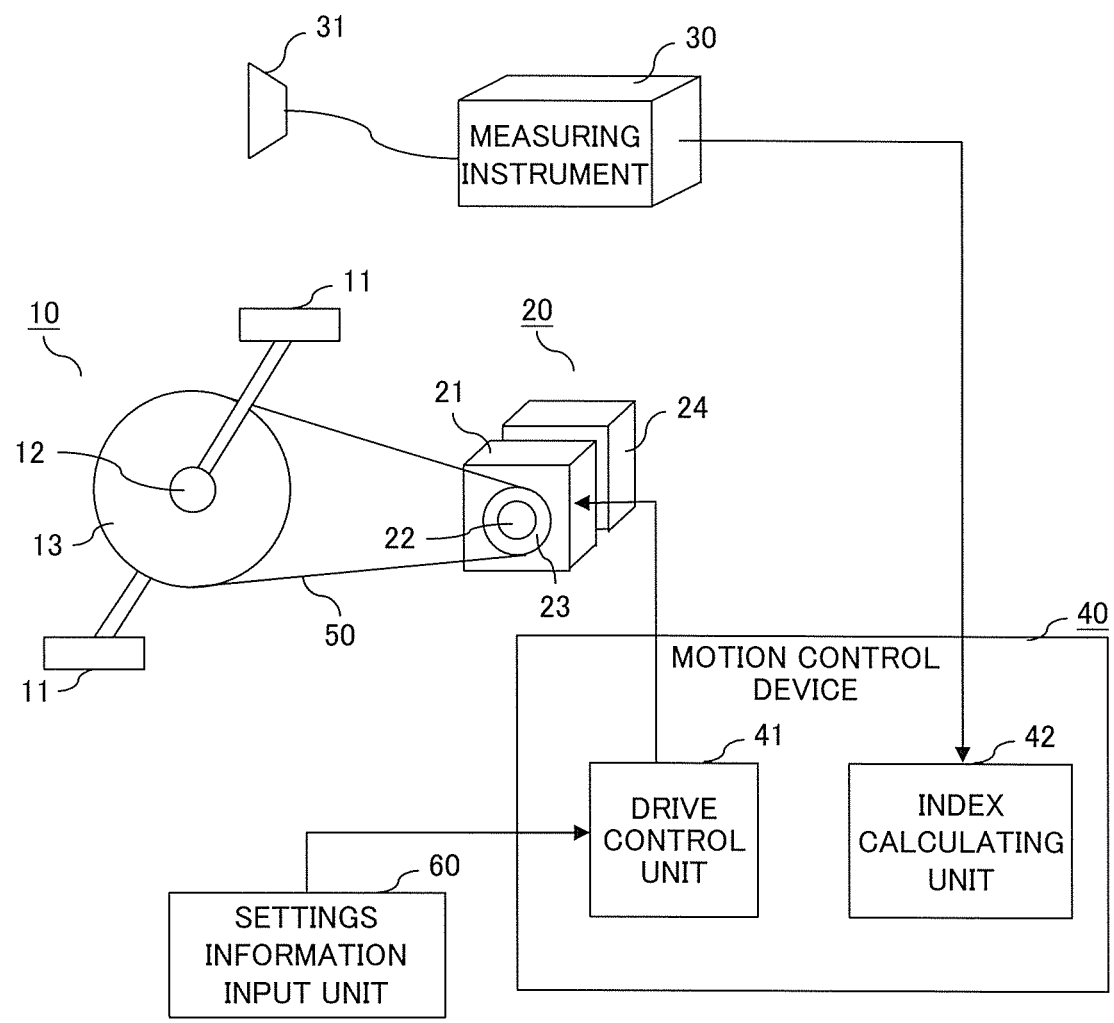
FIG. 1 is a diagram for illustrating the configuration of a kinesitherapy apparatus according to a first embodiment of the present invention.

FIG. 1 is a diagram for illustrating the configuration of a kinesitherapy apparatus according to a first embodiment of the present invention. In FIG. 1, a bicycle ergometer, which corresponds to the kinesitherapy apparatus, includes a pedaled rotational mechanism 10 to be operated (rotated) by a user, a rotating electrical machine 20, a measuring instrument 30, and a motion control device 40.

The pedaled rotational mechanism 10 is provided with a pair of pedals 11, a pedal rotation shaft 12, which is linked to each pedal 11, and a pedal-side pulley 13, which is fixed to the pedal rotation shaft 12.

The rotating electrical machine 20 is provided with a rotating electrical machine main body 21, an electrical machine rotation shaft 22, which is driven by the rotating electrical machine main body 21, a load-side pulley 23, which is fixed to the electrical machine rotation shaft 22, and a speed detector 24. The speed detector 24 can be used to measure the self-weight of the feet, and details thereof are described later.

An endless belt (transmission mechanism) 50 is wound around the pedal-side pulley 13 and the load-side pulley 23 to stretch between the pulleys. In other words, the rotating electrical machine 20 is linked to the pedaled rotational mechanism 10 via the belt 50.

The rotating electrical machine 20 is connected to the motion control device 40. The motion control device 40 includes a drive control unit 41, which is configured to control the motion of the rotating electrical machine 20, and an index calculating unit 42, which is configured to calculate the AT serving as an index of exercise tolerance.

The motion control device 40 is a computer that includes a storage unit (a RAM and a ROM) configured to store a program and other types of information, and an arithmetic unit (a CPU) configured to execute arithmetic processing based on information that is stored in the storage unit.

The drive control unit 41 is capable of controlling the motion of the rotating electrical machine 20 as programmed by an exercise stress program for a person with low physical strength. The exercise stress program is selected based on settings information (about, among others, exercise intensities specified on a time axis. The exercise intensities include a minus watt (minus load), for example, an assist load), which is input from a settings information input unit 60.

The drive control unit 41 is also capable of appropriately controlling the motion (position, revolving speed, torque, wattage, and the like) of the rotating electrical machine 20 in each of a resting period, a warm-up period, and a ramp loading period when the AT is calculated.

The rotating electrical machine 20 is configured to generate a load to be applied to the operation of the pedaled rotational mechanism 10 for exercise of a person to be tested. In other words, the rotating electrical machine 20 operates as a generator when a load is generated. The rotating electrical machine main body 21 operates as a regenerative load by the pedal operation of the person to be tested. The magnitude of the load generated by the rotating electrical machine 20 can be changed freely by changing the magnitude of a load current.

A mask 31 configured to measure the oxygen uptake, carbon dioxide emission, and ventilation volume of the person to be tested per breath is connected to the measuring instrument 30. When an exercise stress test is conducted, the person to be tested wears the mask 31 and pushes the pedals 11, and the measuring instrument 30 measures the oxygen uptake, carbon dioxide emission, and ventilation volume per breath in each period in order to calculate/measure the minute oxygen uptake, the minute carbon dioxide emission, and the minute ventilation volume.

A technical feature of the present invention resides in that the calculation of a more stable AT is accomplished by increasing the amount of measurement data measured at points below the AT. The amount of measurement data measured at points below the AT is increased by measuring the minute oxygen uptake, the minute carbon dioxide emission, and the minute ventilation volume in a state without muscle activity (oxygen consumption) that occurs when a warm-up is performed at zero watts (0 W) (a state where oxygen consumption due to muscle activity does not occur). This state is reached by achieving a minus load state where a minus load as an assist load is applied through the power running operation of the rotating electrical machine main body 21 in the warm-up period when an exercise stress test is conducted, and starting a ramp loading test from the minus load state.

In order to clarify this technical feature, the related art that calculates the AT by applying a constant plus-watt load or a zero-watt (0 W) load in a warm-up period is described first.

Figure 2B:
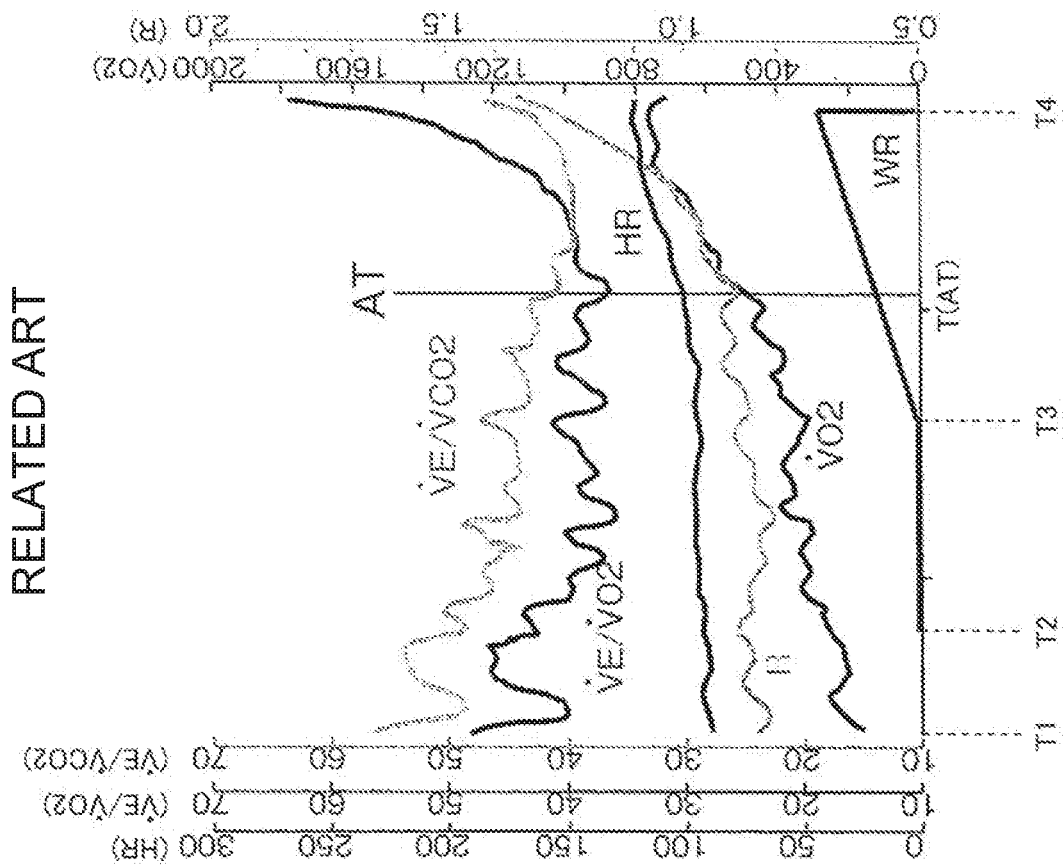
FIG. 2A and FIG. 2B are graphs for showing transitions of measurement data that includes minute oxygen uptake and minute carbon dioxide emission and that is used to calculate an AT by a kinesitherapy apparatus of the related art.
Figure 2A:
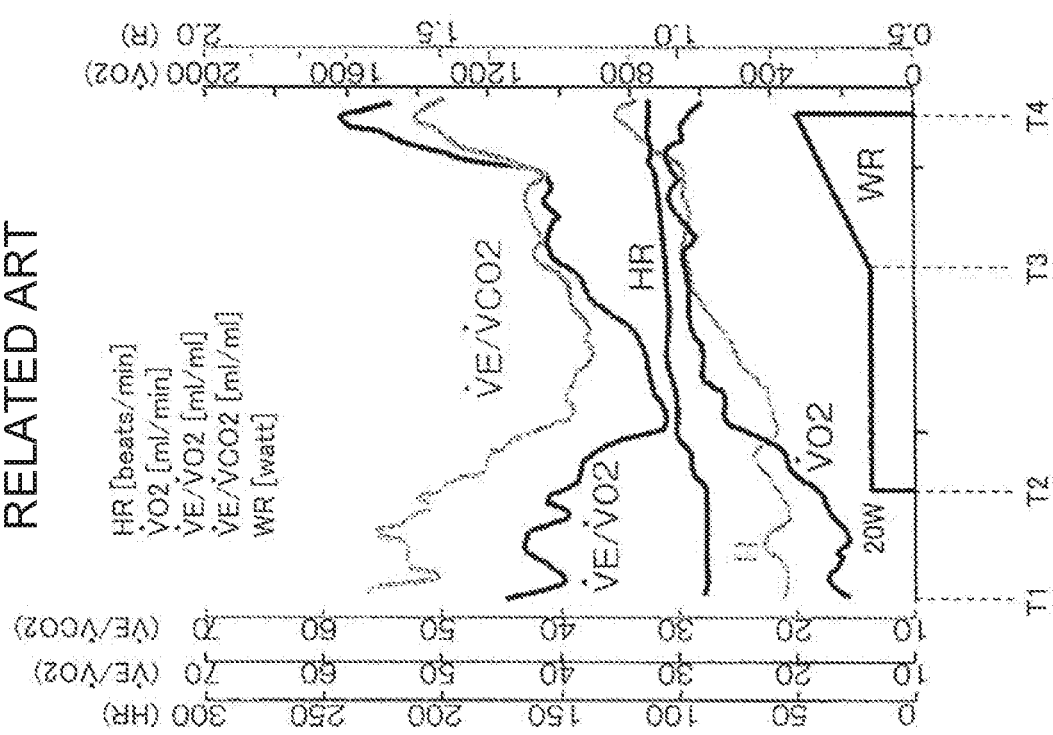

FIG. 2A and FIG. 2B are graphs for showing transitions of measurement data that includes the minute oxygen uptake and the minute carbon dioxide emission and that is used to calculate the AT by a kinesitherapy apparatus of the related art. In FIG. 2A and FIG. 2B, the horizontal axis represents time and the vertical axis represents the magnitude of each piece of measurement data. The measurement data shown in FIG. 2A and FIG. 2B is an example of data that is measured when the person to be tested is a person with low physical strength.

A section from T1 to T2 represents a resting period, a section from T2 to T3 represents a warm-up period, and a section from T3 to T4 represents a ramp loading period. In FIG. 2A, the load in the warm-up period is set to a plus-watt load of 20 W. In FIG. 2B, on the other hand, the load in the warm-up period is set to 0 W.

The V-slope method is capable of expressing only the relation between the minute oxygen uptake and the minute carbon dioxide emission at points above the AT (which means that there is no point of inflection or no point of turning). The description therefore deals with a trend method that uses $VE/VO_2$ and $VE/VCO_2$.

The minute oxygen uptake, the minute carbon dioxide emission, and the minute ventilation volume are measured in the ramp loading period in order to calculate $VE/VO_2$ and $VE/VCO_2$. In the case where a point at which $VE/VCO_2$ does not increase but $VE/VO_2$ increases is successfully identified, this point of inflection can be calculated as the AT of the person to be tested.

When a load of 20 W is applied in the warm-up period as in FIG. 2A, the person to be tested needs to push the pedals 11 in the warm-up period so as to overcome the 20-watt load. It is assumed here that the person to be tested is a person with low physical strength, and that the load at a point corresponding to the AT is around 20 W, or equal to or less than 20 W.

In this case, while there is already no increase in $VE/VCO_2$ in the warm-up period as shown in FIG. 2A, measurement data that indicates an increase in $VE/VO_2$ is unfortunately obtained. Consequently, an accurate point of inflection cannot be obtained from measurement data in the ramp loading period, which results in a failure to obtain the AT.

A solution to this is to set the load in the warm-up period to 0 W as in FIG. 2B, and the point of inflection can now be obtained from measurement data in the ramp loading period. The index calculating unit 42 can consequently obtain the AT at a point where the time is T (AT).

The kinesitherapy apparatus having the configuration of FIG. 1 needs to take into account mechanical friction that is generated by a mechanical structure made up of the pedaled rotational mechanism 10, the belt 50, the rotating electrical machine 20, and others. The drive control unit 41 therefore accomplishes a load of 0 W through the power running control of the rotating mechanical machine main body 21 so that a driving force (assisting force) equivalent to the mechanical friction is generated by the rotating electrical machine 20.

In the case of a person with low physical strength, however, a measurement time corresponding to an interval from T3 to T(AT) is short despite the 0-watt load set to the warm-up period as in FIG. 2B. In addition, although measurement points can be increased until the AT is reached by changing the ramp loading from, for example, 10 W/min. to 5 W/min., there is an appropriate ramp load that is appropriate for metabolism adjustment and the length of the exercise time as discussed in a Japanese translation of "Principles of Exercise Testing and Interpretation" written by Wasserman, K., Hansen, J. E., Sue, D. Y., et al., translated by Koichi Taniguchi and Takayoshi Yoshida, and published in Tokyo by Nankodo in 1990 (pp. 78-96), and Hiroaki Tatsuki et al., "Estimation of Exercise Intensity and Ramp Load in Cardiopulmonary Exercise Testing Using the Maximum Walking Speed in Elderly Hospitalized Patients with Acute Coronary Syndrome", Journal of Rural Medicine, Volume 65, Issue 2, Page 203, July 2016. This sometimes results in a difficulty in calculating the AT with precision based on a sufficient number of pieces of sampling data.

In the case where the person to be tested is a patient who has heavy lower limbs, for example, an obese patient, the metabolism in the warm-up period is large even at a load of 0 W, and there is a fear that the minute oxygen uptake ($VE/VO_2$) and the minute carbon dioxide emission ($VE/VCO_2$) rise during the zero-watt warm-up period. This also can be one of cases where calculating the AT with precision is difficult despite the load in the warm-up period being set to 0 W.

The present invention accomplishes the calculation of a stable AT by achieving a minus load state where a minus load is applied as an assist load through the power running operation of the rotating electrical machine main body 21 in the warm-up period, and starting a ramp loading test from the minus load state.

The minus load is a load at which a person to be tested who puts his or her feet on the pedals 11 can rotate the pedals 11 in a normal pedaling direction, without pedaling with force. A specific numerical value that is set as the minus load is, for example, minus 20 watt (−20 W).

In the present invention, a warm-up is performed at the minus watt and ramp loading is executed with the minus watt as the starting point. For instance, a warm-up is performed at −20 W and the ramp loading period is started from −20 W. In the beginning of the ramp loading period, the pedals 11 rotate voluntarily through the power running operation, while the person to be tested keeps the muscles in his or her legs relaxed.

When the person to be tested performs a warm-up at a minus watt (minus load), the pedals 11 rotate on their own requiring little muscle activity (an increase in oxygen uptake from the level in the resting period), and the person to be tested is not really exercising. A situation where metabolism becomes large before the ramp loading period is started can accordingly be avoided, even when the person to be tested is an obese person.

The same phenomenon takes place also after the ramp loading period is started, as long as torque equivalent to the self-weight of the feet is assisted. The revolving speed of the pedals drops as the load increases gradually from the minus watt (minus load). The pedals stop rotating at a time point where the self-weight of the feet matches the assist torque. Thereafter, a regenerative load is set which, in spite of being a minus watt (minus load), requires the person to be tested to pedal.

A ramp load is then applied to the pedals 11 gradually, thereby requiring the person to be tested to pedal with a force that fights against the load of the pedals 11 so that the pedals 11 are rotated at a constant revolving speed. In the ramp loading period, the index calculating unit 42 measures the minute oxygen uptake and the minute carbon dioxide emission at regular intervals based on measurement data that is obtained from the measuring instrument 30.

The index calculating unit 42 is capable of obtaining the AT as a point of inflection by creating a graph from the minute oxygen uptake and the minute carbon dioxide emission that are measured over the ramp loading period, with one of the minute oxygen uptake and the minute carbon dioxide emission as the vertical axis and the other as the horizontal axis. The point of inflection is described later with reference to FIG. 5.

Figure 3:
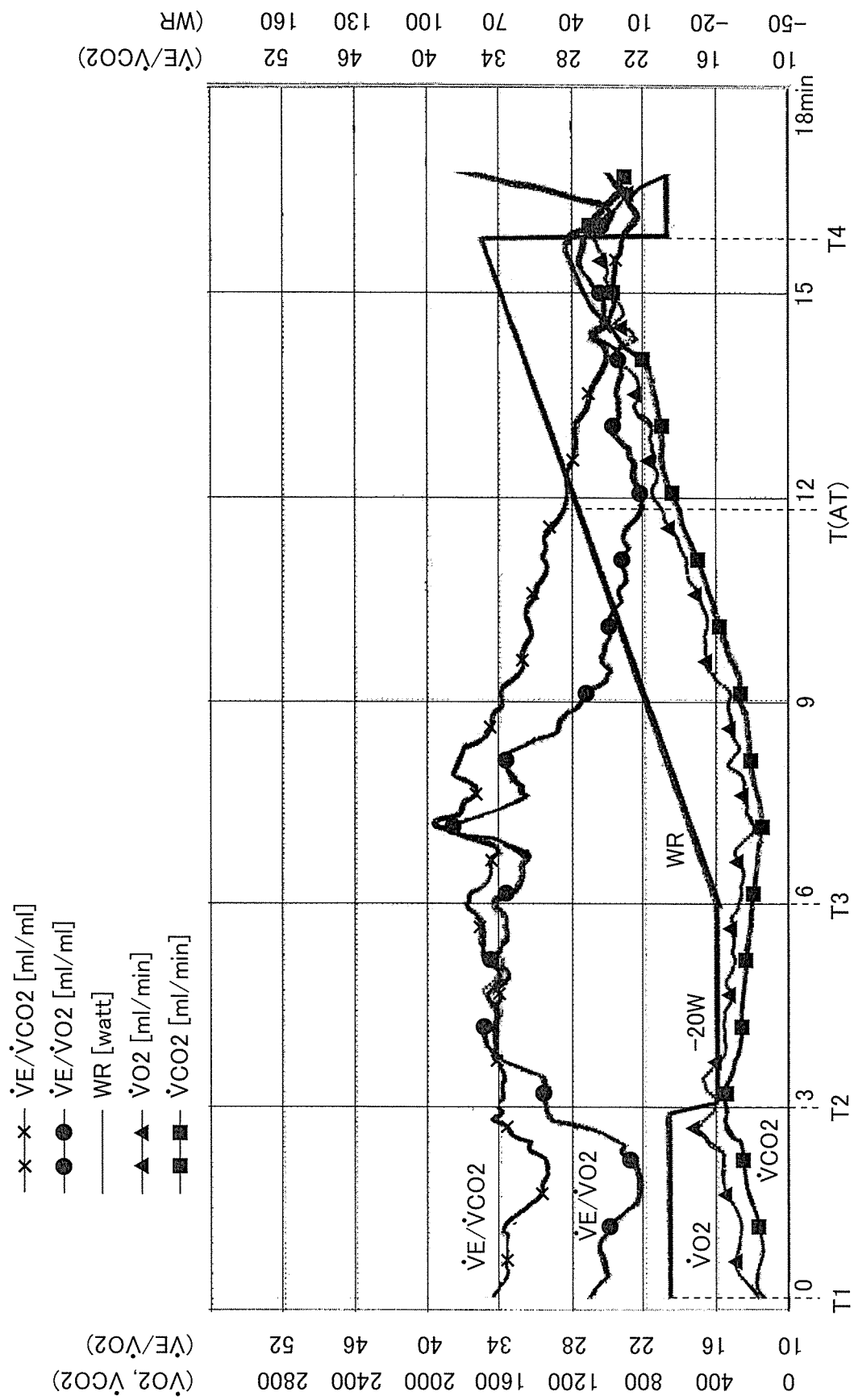
FIG. 3 is a graph for showing transitions of measurement data that includes the minute oxygen uptake and the minute carbon dioxide emission and that is used to calculate the AT by the kinesitherapy apparatus according to the first embodiment of the present invention.

FIG. 3 is a graph for showing transitions of measurement data that includes the minute oxygen uptake and the minute carbon dioxide emission and that is used to calculate the AT by the kinesitherapy apparatus according to the first embodiment of the present invention. A person to be tested who provides the measurements of FIG. 3 is an able-bodied person, and detailed data on the person to be tested is as follows:

Gender: Female
Age: 31 years old
Weight: 48 kg
Height: 155 cm

In FIG. 3, a 3-minute resting period is followed by a 3-minute warm-up period in which the minus load is set to −20 W and, in a ramp loading period that follows the warm-up period, each type of data is measured while increasing the load in a ramp pattern at a rate of 10 W/min.

In FIG. 3, a state where the person to be tested pushes the pedals 11 with force is started around −5 W, and a point of inflection is obtained around 38 W. By performing a warm-up at a minus load, for example, −20 W, and starting the ramp loading period with the minus load as the starting point in this manner, an interval from the start of the warm-up to the obtainment of the AT (the interval from T3 to T(AT)) is widened from the one in the related art (the ramp loading period in the related art is started from 0 W).

A point of inflection corresponding to the AT can consequently be identified from more pieces of sampling data with respect to the minute oxygen uptake and the minute carbon dioxide emission, thereby improving the precision of AT calculation.

Figure 4:
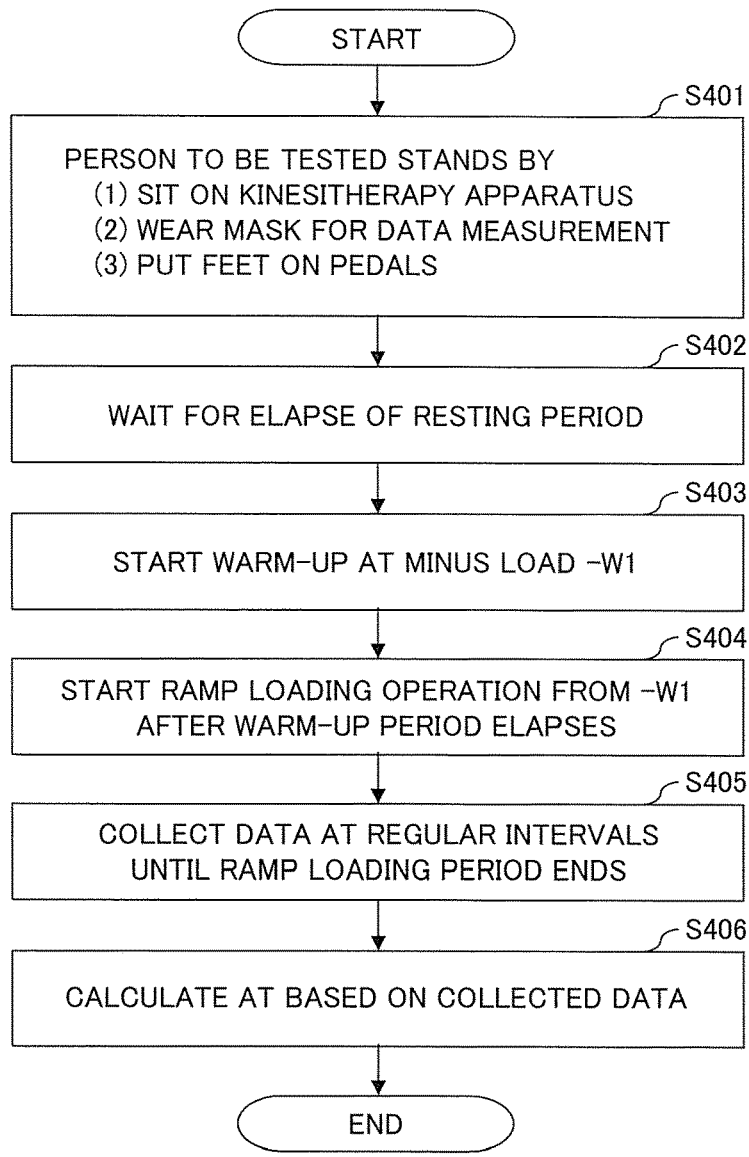
FIG. 4 is a flow chart for illustrating an anaerobic threshold identifying method that is executed in the kinesitherapy apparatus according to the first embodiment of the present invention.

A description is given next with reference to a flow chart on a series of processing steps that is executed when the AT is calculated by the kinesitherapy apparatus according to the first embodiment of the present invention, including the motions of a person to be tested. FIG. 4 is a flow chart for illustrating an anaerobic threshold identifying method that is executed in the kinesitherapy apparatus according to the first embodiment of the present invention.

In Step S401, a person to be tested of the exercise stress test first performs the following three motions, and stands by until the exercise stress test is started:

(1) The person to be tested sits on the kinesitherapy apparatus.

(2) The person to be tested wears on his or her face the mask 31, which is used to measure the minute oxygen uptake and the minute carbon dioxide emission.

(3) The person to be tested puts his or her feet on the pedals 11.

After the three motions are completed, activation operation is performed by, for example, the person to be tested, at which point the processing proceeds to Step S402. In Step S402, the loading apparatus does not move and confirms that there is no particular change in the condition of the person to be tested by measuring the subject's minute oxygen uptake, minute carbon dioxide emission, and minute ventilation volume during a rest. The processing proceeds to Step S403 upon elapse of the resting period.

In Step S403, the drive control unit 41 performs power running control on the rotating electrical machine main body 21 at a minus load (for example, −20 W) to start the warm-up period. This enables the person to be tested to warm up without pedaling with force, and the warm-up is completed while the minute oxygen uptake and the minute carbon dioxide emission by which metabolism is evaluated drop down to the level observed during the rest.

In Step S404, after the warm-up period having a predetermined length elapses, the drive control unit 41 starts the ramp loading period in which the load is increased in constant increments (for example, 10 W/min.) determined in advance, with the minus load as the starting point. In this manner, the interval from the start of the ramp loading period till the AT is obtained can be set wider than in the related art.

In Step S405, the index calculating unit 42 calculates, via the measuring instrument 30, the minute oxygen uptake, the minute carbon dioxide emission, and the minute ventilation volume at regular intervals over the predetermined length of the ramp loading period to obtain time-series data.

Figure 5:
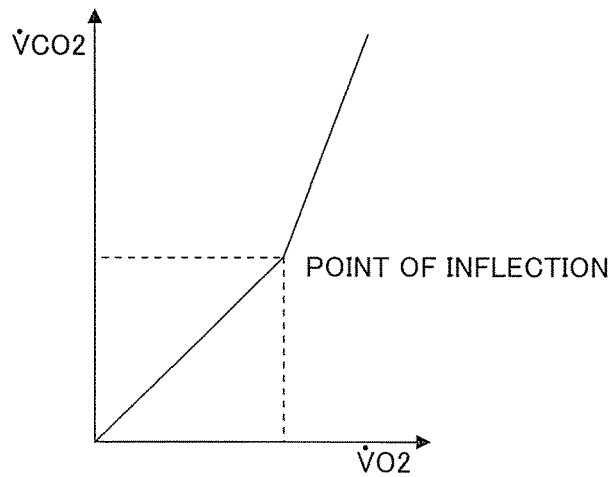
FIG. 5 is a graph for showing how to obtain a point of inflection from time-series measurement data of the minute oxygen uptake and time-series measurement data of the minute carbon dioxide emission in the first embodiment of the present invention.

In Step S406, the index calculating unit 42 obtains the AT by identifying the point of inflection or the point of turning from the time-series data of the minute oxygen uptake and the time-series data of the minute carbon dioxide emission. FIG. 5 is an explanatory diagram for obtaining the point of inflection or the point of turning by the V-slope method from time-series measurement data of the minute oxygen uptake and time-series measurement data of the minute carbon dioxide emission in the first embodiment of the present invention.

FIG. 5 is a graph of two types of time-series measurement data with the vertical axis representing the minute carbon dioxide emission and the horizontal axis representing the minute oxygen uptake. The case shown in FIG. 5 as an example is an ideal case. An area to the left of the point of inflection is an aerobic exercise area in which the minute oxygen uptake and the minute carbon dioxide emission increase at a proportion of substantially 1:1.

An area to the right of the point of inflection, on the other hand, is an anaerobic exercise area in which carbohydrate metabolism takes place in addition to lipid metabolism, thereby raising the proportion of increase in minute carbon dioxide emission, and the point of inflection or the point of turning like the one shown in FIG. 5 is obtained as a value corresponding to the AT.

As described above, a feature of the present invention is that the precision of AT calculation is improved by starting the ramp loading period from a minus load and thus obtaining more pieces of measurement data for calculating the AT than in the related art. Therefore, it suffices that the minus load has a value at which a power running current that is larger than at least a current equivalent to mechanical friction can be caused to flow.

The present invention is also capable of setting a wider interval from the start of the ramp loading period to the time when the AT is obtained by identifying the value of the minus load while taking into account torque that is equivalent to the self-weight of the feet of the person to be tested, in addition to torque that is equivalent to the mechanical friction. This minus load grows in importance as the AT becomes lower, and helps to grasp the AT accurately for a post-surgery patient with low physical strength, an obese patient, an elderly patient with cardiac failure, and the like.

The description given above on the first embodiment deals with a case in which a value that is even larger than the combined value of the torque equivalent to the mechanical friction and the torque equivalent to the self-weight of the feet of the person to be tested is set as the minus load, and the ramp loading period is started from the thus set minus load. However, the AT calculation method according to the present invention is not limited thereto.

For example, the motion control device 40 may identify a load at which the pedals 11 no longer rotate when the load is increased gradually from −20 W toward 0 W as a minus load suited to the person to be tested that corresponds to the combined value of the torque equivalent to the mechanical friction and the torque equivalent to the self-weight of the feet of the person to be tested. The motion control device 40 can determine the rotation state of the pedals 11 from the detection result of the speed detector 24.

After the minus load suited to the person to be tested is calculated, the ramp loading period is started in which the load is increased in constant increments determined in advance, with the value of this minus load as an initial value of the ramp loading period. This method is capable of enhancing the precision of AT calculation as the specific calculation method described in the first embodiment is. In this case, the amount of change in load that is used when a motion for identifying a minus load suited to the person to be tested is performed can be set to an optimum value independently of the amount of change in load in the ramp loading period.

Conversely, the motion control device 40 may identify a load at which the pedals 11 start rotating when the load is decreased gradually from 0 W in a minus direction as a minus load suited to the person to be tested that corresponds to the combined value of the torque equivalent to the mechanical friction and the torque equivalent to the self-weight of the feet of the person to be tested.

A minus load suited to the person to be tested can be identified also by grasping a minus load at which the pedals 11 start moving when the minus load is applied gradually at the time of transition from the resting period to the warm-up period.

After the minus load suited to the person to be tested is calculated, the ramp loading period is started in which the load is increased in constant increments determined in advance, with the value of this minus load as an initial value of the ramp loading period. This method is capable of enhancing the precision of AT calculation as the specific calculation method described in the first embodiment is. In this case also, the amount of change in load that is used when a motion for identifying a minus load suited to the person to be tested is performed can be set to an optimum value independently of the amount of change in load in the ramp loading period.

It is said that the self-weight of the feet is normally about 10% of the body weight. The minus load may therefore be identified by assuming 10% of the body weight of the person to be tested as the self-weight of the feet of the person to be tested.

As described above, the kinesitherapy apparatus and the anaerobic threshold identifying method according to the first embodiment include a configuration to calculate the AT from time-series measurement data of the minute oxygen uptake and time-series measurement data of the minute carbon dioxide emission that are measured in a ramp loading period by starting the ramp loading period from a state where a power running current larger than one equivalent to mechanical friction is caused to flow. As a result, an interval from the start of the ramp loading period to a time point that corresponds to the AT can be set wider than in the related art, and the AT can consequently be obtained from a larger number of pieces of measurement data with high precision.

In addition, a change in metabolism in the warm-up period can be suppressed by setting a minus load that takes into account the self-weight of the feet of the person to be tested. As a result, appropriate measurement data is obtained in the ramp loading period and the AT can be obtained with high precision.

In addition, the AT obtained with high precision can be used to, for example, help reduce obesity by allowing an obese patient with low physical strength to follow a reasonable exercise program that alternates anaerobic exercise with aerobic exercise as far as the patient's physical strength permits.

What is claimed is:

1. A kinesitherapy apparatus, comprising:
   a measuring instrument configured to measure oxygen uptake and carbon dioxide emission of a person with low physical strength to be tested;
   a pedaled rotational mechanism to be operated by the person to be tested;
   a rotating electrical machine that is linked to the pedaled rotational mechanism via a transmission mechanism and is configured to generate an assist load to be applied to the operation of the pedaled rotational mechanism; and
   a motion control device configured to control a motion of the rotating electrical machine as programmed by an exercise stress program for the person with low physical strength and to calculate an anaerobic threshold,
   wherein the motion control device is configured to, when conducting a kinesitherapy test on the person, (1) control the rotating electrical machine to (1a) generate a minus assist load in a warm-up period and (1b) raise a load at a constant increment from a starting point to a regenerative load in a ramp loading period, which follows the warm-up period, and (2) calculate the anaerobic threshold based on time-series data of respiratory metabolism comprising the oxygen uptake, the carbon dioxide emission, and ventilation volume, which are obtained via the measuring instrument during the ramp loading period,
   wherein the minus assist load has an initial value that overcomes torque equivalent to mechanical friction caused by a mechanical structure comprising the pedaled rotational mechanism, the transmission mechanism, and the rotating electrical machine,
   wherein the initial value of the minus assist load overcomes a combined value of torque equivalent to the mechanical friction and torque equivalent to a self-weight of feet of the person to be tested and causes rotation of pedals of the pedaled rotational mechanism, and
   wherein the motion control device is further configured to (1) after the warm-up period, increase gradually a value of the minus assist load, (2) identify a value of the generated minus assist load at which the person to be tested is not pushing the pedals with force and the rotation of the pedals is stopped, and (3) start the ramp loading period with the identified value of the minus assist load as the starting point.

2. The kinesitherapy apparatus according to claim 1, wherein the rotating electrical machine comprises:
   a rotating electrical machine main body;
   an electrical machine rotation shaft configured to be driven by the rotating electrical machine main body; and
   a load-side pulley fixed to the electrical machine rotation shaft.

3. The kinesitherapy apparatus according to claim 2, wherein the rotating electrical machine further comprises a speed detector.

4. The kinesitherapy apparatus according to claim 1, wherein the motion control device comprises:
   a storage unit configured to store a program and other types of information; and
   an arithmetic unit configured to execute arithmetic processing based on information that is stored in the storage unit.

5. The kinesitherapy apparatus according to claim 4, wherein the rotating electrical machine comprises:
   a rotating electrical machine main body;
   an electrical machine rotation shaft configured to be driven by the rotating electrical machine main body; and
   a load-side pulley fixed to the electrical machine rotation shaft.

6. An anaerobic threshold identifying method for calculating an anaerobic threshold by conducting a kinesitherapy test on a person with low physical strength using a kinesitherapy apparatus,
   the kinesitherapy apparatus comprising:
   a measuring instrument configured to measure oxygen uptake and carbon dioxide emission of the person to be tested;
   a pedaled rotational mechanism to be operated by the person to be tested;
   a rotating electrical machine that is linked to the pedaled rotational mechanism via a transmission mechanism and is configured to generate an assist load to be applied to the operation of the pedaled rotational mechanism; and
   a motion control device configured to control a motion of the rotating electrical machine as programmed by an exercise stress program for the person and to calculate the anaerobic threshold,
   the anaerobic threshold identifying method, which is executed by the motion control device, comprising:
   controlling the rotating electrical machine to generate a minus assist load in a warm-up period before the anaerobic threshold is calculated, wherein (1) the minus assist load is generated continuously during the warm-up period until the warm-up period ends, (2) the minus assist load has an initial value that overcomes torque equivalent to mechanical friction caused by a mechanical structure comprising the pedaled rotational mechanism, the transmission mechanism, and the rotating electrical machine, and (3) the initial value of the minus assist load overcomes a combined value of torque equivalent to the mechanical friction and torque equivalent to a self-weight of feet of the person to be tested and causes rotation of pedals of the pedaled rotational mechanism;

after the warm-up period, increasing gradually a value of the minus assist load in a plus direction;

identifying a value of the generated minus assist load at which the person to be tested is not pushing the pedals with force and the rotation of the pedals is stopped;

raising a load in a ramp loading period, which follows the warm-up period, from the identified value of the minus assist load, as a starting point of the ramp loading period, at a constant proportion;

obtaining time-series data of the oxygen uptake and time-series data of the carbon dioxide emission in the ramp loading period via the measuring instrument;

obtaining one of a point of inflection and a point of turning by creating a two-dimensional coordinate graph of minute oxygen uptake and minute carbon dioxide emission based on the obtained time-series data; and calculating a load value that corresponds to the one of the point of inflection and the point of turning as the anaerobic threshold.

7. The anaerobic threshold identifying method according to claim 6, wherein the rotating electrical machine comprises:

a rotating electrical machine main body;

an electrical machine rotation shaft configured to be driven by the rotating electrical machine main body; and a load-side pulley fixed to the electrical machine rotation shaft.

8. The anaerobic threshold identifying method according to claim 6, wherein the rotating electrical machine further comprises a speed detector.

9. The anaerobic threshold identifying method according to claim 6, wherein the motion control device comprises:

a storage unit configured to store a program and other types of information; and an arithmetic unit configured to execute arithmetic processing based on information that is stored in the storage unit.

10. The anaerobic threshold identifying method according to claim 9, wherein the rotating electrical machine comprises:

a rotating electrical machine main body;

an electrical machine rotation shaft configured to be driven by the rotating electrical machine main body; and a load-side pulley fixed to the electrical machine rotation shaft.

* * * * *